United States Patent [19]

Spielvogel

[11] Patent Number: 4,709,083

[45] Date of Patent: Nov. 24, 1987

[54] METHOD OF MAKING BORON ANALOGUES

[75] Inventor: Bernard F. Spielvogel, Wake, N.C.

[73] Assignee: The United States of America as represented by the Secretary of the Army, Washington, D.C.

[21] Appl. No.: 864,612

[22] Filed: May 19, 1986

[51] Int. Cl.$^4$ ............................................. C07C 69/76
[52] U.S. Cl. .................................. 560/110; 560/105; 560/253; 560/61; 564/281; 564/292; 564/293
[58] Field of Search ................. 560/105, 110, 253, 61; 564/281, 292, 293

[56] References Cited

PUBLICATIONS

Mancilla, T. et al., Tetrahedron Left 23(15), 1561–4, 1982.
Brown, H. C., Inorg. Chem. (23), 18, 2746–53, 1984.

*Primary Examiner*—Paul J. Killos
*Attorney, Agent, or Firm*—Peter A. Taucher; Gail S. Soderling

[57] ABSTRACT

A method of synthesizing boron analogues of choline and choline related materials is disclosed. The method comprises reacting N,N dimethylethanolamine with hydrogen chloride or an acid chloride to form an ester hydrochloride. The resulting aminoalcohol hydrochloride or ester hydrochloride is further reacted with tetraethyl NBH$_4$.

Also disclosed are pharamaceutically interesting compounds of acetylcholine.

10 Claims, No Drawings

METHOD OF MAKING BORON ANALOGUES

GOVERNMENT INTEREST

The invention described herein may be manufactured, used, and licensed by or for the Government for governmental purposes without payment to me of a royalty thereon.

In one aspect this invention relates to biologically interesting compounds related to choline and choline analogues such as acetylcholine. In a further aspect this invention relates to boron compounds. In yet a further aspect, this invention relates to methods of forming boron compounds.

The synthesis of various compounds which are analogues of various biologically active compounds are of interest for use in studying biochemical events at the molecular level. In pursuit of this goal various esters of boron analogues of amino acids, U.S. Ser. No. 664,647 filed Oct. 25, 1984 were disclosed.

The present invention relates to a high yield, two step method for generating a class of boron analogues related to choline type molecules. The inventive process has a first step comprising reacting N,N dimethylethanolamine with hydrogen chloride or an acid chloride. The first step in the synthesis results in an ester hydrochloride or in the case of HCl, the aminoalcohol hydrochloride which can be separated from the reaction mixture. The resulting ester hydrochloride is further reacted with $Et_4NBH_4$ to form a boron compound having the general structure $H_3B(CH_3)_2NCH_2CH_2OR$ where R is hydrogen or an acyl (R'CO) group.

In greater detail the process of this invention uses a first reaction sequence to form an ester hydrochloride of the desired boron analogue. This first reaction uses N,N dimethylethanolamine as an initial reactant which is dissolved in a diluent such as ether or dichloromethane. The first reaction step is mild but does not require additional heating so the reaction can be carried out in a chilled vessel at about 0° C. to room temperature. If desired, the reaction vessel can be maintained under a nitrogen atmosphere to prevent any extraneous reactions between the reactants and the resulting products.

The N,N dimethylethanolamine is reacted with hydrogen chloride or an organic acid chloride having the general formula R—Cl where R is chosen from the class consisting of hydrogen and acyl(R'CO—). Examples of suitable organic components R' of the acylgroup include lower alkyl having 1 to 6 carbon atom i.e., methyl, ethyl, propyl, isopropyl; aryl, alkaryl and arylakyl specific examples including: $CH_3CO$—, $C_6H_5OCH_2CO$—, $C_6H_5CH_2CO$—, suberyl, and $C_6H_5CO$—. The resulting ester hydrochloride provides an intermediate product suitable for further processing to the desired end products. It is expected that under normal conditions a yield of about 85–95% will be obtained by the reaction.

The amine-organic acid chloride reaction is preferably carried out in an anhydrous solvent since the ester hydrochlorides of the initial reaction are generally extremely hydroscopic and contact with water would be detrimental. Suitable solvents include anhydrous ether or dichloromethane. The resultant ester hydrochloride is separated from the solvent and purified by repeated washings using anhydrous ether under a nitrogen atmosphere.

Purification can be carried out by recrystalization from a solvent mixture or by column chromatography.

The purified ester hydrochloride is converted to the desired boron analogue by reacting with $Et_4NBH_4$ in a dichloromethane solution.

EXAMPLE 1

Preparation of 2-(hydroxyethyl)dimethylamine-borane

A solution of 1.5 mol N,N dimethylethanolamine (133.71 g) was formed in 100 ml ether at 0° C. Two moles (72 g) of dry HCl in 400 ml of ether was added to the amine solution in drops over a two hour period with vigorous stirring. White fumes and some precipitate were formed immediately. The cloudy suspension was stirred for about 1 hour after the HCl addition and the reaction mixture filtered under a dry nitrogen atmosphere.

The salt was repeatedly washed with anhydrous ether and vacuum pumped overnight to yield 156.8 g (83% yield) of 2-(hydroxyethyl) dimethylammonium chloride.

0.03 mol (3.7 g) of the above product was added to 300 ml of dichloromethane with stirring. Solid $Et_4NBH_4$, 0.034 mol (5 g) was slowly added to the solution and the reaction mixture stirred for 2 hr at ambient temperature. An initial vigorous evolution of hydrogen took place. The reaction mixture was refluxed overnight.

The refluxed reaction mixture was cooled and filtered. The filtrate was washed 3 times with 100 ml of water and dried over magnesium sulfate. The solvent was removed under reduced pressure yielding 1.2 g (40.2%) of a clear oily material.

NMR data confirmed the compound was 2(hydroxyethyl)dimethylamine-borane.

EXAMPLE 2

Preparation of 2 (Acetoxyethyl)dimethylamine-borane

A solution of MeCOCl 17.27 g (0.22 mol) in 100 ml dichloromethane was added by drops to a solution containing 17.83 g (0.2 mol) N,N dimethylethanolamine in 100 ml of dichloromethane which was at 0° C. The addition was done over a one hour period. White fumes were produced immediately. The reaction mixture was stirred continuously overnight at ambient temperature. The solvent was removed under vacuum, and the solids repeatedly washed with anhydrous ether. The solids 30.6 g (91%) were dried under vacuum overnight. IR spectral analysis confirmed the solid was 2-(acetoxyethyl)dimethylammonium chloride.

A solution of 3.80 g (0.23 mol) of the esterhydrochloride was formed with 300 ml dichloromethane at room temperature. To the stirred solution 4.94 g (0.034 mol) of solid $Et_4NBH_4$ was added slowly. An initial vigorous evolution of hydrogen ensued. After the reaction subsided, the mixture was refluxed for 3 hours. The refluxed reaction mixture was cooled, washed with water (3×100 ml), dried over $MgSO_4$, concentrated and dried under vacuum.

The product was a slightly yellowish liquid. A yield of 2.8 g (85% yield) was achieved. An NMR spectra confirmed that the product was 2-(acetoxyethyl)dimethylamine-borane.

EXAMPLE 3

Preparation of 2-(phenylacetoxyethyl)dimethylamine borane

A solution containing 8.91 g (0.1 mol) N,N dimethylethanolamine was formed by stirring the amine into 200 ml of dichloromethane at 0° C. To the solution was add 15.46 g (0.1 mol) of $C_6H_5COCl$ in 50 ml of ether. The phenol containing solution was dropped in the amine solution over a 1 hour period while maintaining the reaction at 0° C. White fumes and a white precipitate were formed. The suspension was stirred at room temperature for 5 hours, filtered and the filtrate repeatedly washed with ether. The ether washings were concentrated and kept in a freezer to collect additional product. The total solids yielded 21.7 g (89%) was recrystalized from a dichloromethane/ether solvent in a freezer to a final yield of 18.28 g (75%) of a purplish solid, 2-(phenylacetoxyethyl)dimethylammonium chloride.

A solution of the 2-(phenylacetoxyethyl)dimethylammonium chloride was formed using 21.7 g (0.089 mol) in 450 ml of dichloromethane and 14.21 g (0.098 mol) of $Et_4NBH_4$ was added to the solution of 0° C. while stirring the solution. The refluxed reaction mixture was kept under a nitrogen atmosphere and stirred continuously for 2 hrs and then refluxed overnight. The solution was cooled, washed with water (3×100 ml), dried over magnesium sulfate and concentrated to yield 16.3 g (83% yield) of 2 (phyenylacetoxyethyl)dimethylamine borane. The crude product was purified by column chromatography on a silica gel column eluted with $CH_2Cl_2$. The identity of the compound was confirmed by NMR analysis.

This example shows the use of an aromatic substituent in the borane compound. Also ether was used as a reaction solvent.

EXAMPLE 4

Preparation of 2-(benzoyloxyethyl)dimethylamine-Borane

To a stirred solution of 17.83 g (0.2 mol) of N,N dimethyethanolamine in 200 ml of dichloromethane at 0° C. was added 30.93 g (0.22 mol) of $C_6H_5COCl$ in 200 ml of dichloromethane over a one hour period. The resulting reaction mixture was stirred overnight at ambient temperature. The solvent was removed under reduced pressure and the remaining white solid washed with ether and dried under vacuum. IR spectral analysis confirmed the white solid was 2-(benzoyloxyethyl)-dimethylammonium chloride.

A solution containing 31.4 g (0.13 mol) of the ester hydrochloride in 500 ml of dichloromethane was formed at room temperature. To the solution was add 21.82 (0.15 mol) of solid $Et_4NBH_4$ with stirring. After the original vigorous evolution of hydrogen, the reaction mixture was refluxed overnight. The reaction mixture was cooled, washed with water (3×150 ml), dried over $MgSO_4$ and concentrated. The result was 18 g of a semisolid material containing two reaction products. The semisolid was dissolved in 300 ml of pentane and cooled in a freezer to separate out the borane. The borane was recrystalized from dichlromethane/pentane as white needles.

This example shows the formation of an aromatic borane compound.

A hyperlipidemic screen was performed using the compounds of Examples 2 and 4. The compounds were suspended in 1% aqueous carboxymethylcellulose and adimistered to male $CF_1$ mice intraperitoneally for 16 days at a dosage of 20 mg/kg day.

On days 9 and 16 blood was obtained by tail vein bleeding and the serum separated by centrifugation for 3 min.

Serum cholesterol levels were determined using a modification of the Liebermann-Burchard reaction, see Ness et al, *Clin. Chim. Acta,* v. 10, p. 229, (1964). Serum triglicerides were determined using the Fisher, Hycel Triglyceride Test Kit, a commercially available kit. The results are tabulated in Table 1 below.

TABLE 1

| COM-POUND | SERUM CHOLESTEROL INHIBITION % | | TRIGLYCERIDE INHIBITION % |
|---|---|---|---|
| | 9th Day | 16th Day | 16th Day |
| Example 2 | 28 | 41 | 32 |
| Example 4 | 31 | 37 | 31 |

The reduction in cholesterol and triglycerides shows the compounds provide control of serum and triglceride levels in animals.

EXAMPLE 5

Preparation of (2-acetoxypropyl)dimethylamine-Borane

An aminoalcohol,

was reacted with an acetylchloride in ethyl ether over night to form the ester chloride. The resulting ester chloride was a white, extremely hygroscopic powder.

To provide a better reactant for further processing, the ester hydrochloride was recrystallized from dichloromethane/ethyl ether to provide a pure cholinechloride material.

The purified chloride was dissolved in dichloromethane and solid $Et_4NBH_4$ added under an atmosphere of nitrogen. The reaction mixture was stirred for 3 hours to give a pure choline boron compound

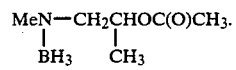

This example shows the preparation of acyl (RCO) choline compounds.

EXAMPLE 6

Preparation of (2-acetoxypropyl)dimethylamine-borane

A solution of 10.30 g (100 mmol) of $Me_2NCH_2CH(CH_3)OH$ in 60 ml dry ethyl ether was stirred and 8.61 g (110 mmol) MeC(O)Cl in dry ethyl ether added from a dropping funnel over one hour. While fumes of HCl were initially produced but dissipated and a white precipitate was produced and the mixture stirred overnight. The resulting white solid was purified by recrystallization from dichloromethane and dry ethyl ether at 0° C. The chloride is very hygroscopic and should be stored in a dessicator.

A solution of 6.77 g (37.3 mmol) of the recrystallized ester hydrochloride was dissolved in 300 ml of dry dichloromethane under a nitrogen atmosphere. To the solution was added 8.10 g (55.9 mmol) of $Et_4NBH_4$ and the evolution of hydrogen monitored by an air bubbler. Once the evolution of hydrogen had stopped, the mixture was refluxed for 3 hours. The refluxed mixture was cooled, washed with water (5×100 ml) and dried over sodium sulphate. The result was a yellowish liquid. Analysis by NMR showed the compound was the boron-choline material desired.

I wish it to be understood that I do not desire to be limited to the exact details of construction shown and described for obvious modifications will occur to a person skilled in the art, without departing from the spirit and scope of the appended claims.

What is claimed is:

1. A method of synthesizing boron analogues of choline and choline related materials (acetylcholine and substituted acetylcholines) comprising the steps of:

reacting N,N dimethylethanolamine with hydrogen chloride or an acid chloride of the formula R—Cl where R is an organic radical chosen from the class consisting of hydrogen and organic acyls (R'CO), to form an ester hydrochloride; and reacting the resulting aminoalcohol hydrochloride or ester hydrochloride with $(C_2H_5)_4NBH_4$.

2. The method of claim 1 where the reactants are dissolved in ether.

3. The method of claim 1 where the reactants are dissolved in dichloromethane.

4. The method of claim 1 where R' contains a lower alkyl group having from 1 to 5 carbon atoms.

5. The method of claim 1 where R' contains an alkaryl.

6. The method of claim 1 where R' contains a hydrogen.

7. The method of claim 1 where R' contains an arylkyl.

8. The method of claim 1 where R' contains a phenyl group.

9. The method of claim 1 where R' contains a methyl group.

10. The method of claim 1 where R' is benzoyloxy.

* * * * *